US005723757A

United States Patent [19]

Rocha-Sosa et al.

[11] Patent Number: 5,723,757
[45] Date of Patent: *Mar. 3, 1998

[54] PLANT PROMOTERS SPECIFIC FOR SINK ORGAN EXPRESSION OF GENES

[75] Inventors: Mario Rocha-Sosa, Cuernavaca, Mexico; Uwe Sonnewald, Berlin, Germany; Wolf-Bernd Frommer, Berlin, Germany; Lothar Willmitzer, Berlin, Germany; Marina Stratmann, Berlin, Germany

[73] Assignee: Hoechst Schering AgrEvo GmbH, Berlin, Germany

[ * ] Notice: The term of this patent shall not extend beyond the expiration date of Pat. No. 5,436,393.

[21] Appl. No.: 448,110

[22] Filed: May 23, 1995

Related U.S. Application Data

[63] Continuation-in-part of Ser. No. 995,911, Dec. 22, 1992, Pat. No. 5,436,393, which is a continuation of Ser. No. 454,363, Dec. 21, 1989, abandoned.

[30] Foreign Application Priority Data

Dec. 21, 1988 [DE] Germany .......... 38 43 627.2

[51] Int. Cl.$^6$ .......... A01H 5/00; C12N 15/29; C12N 15/82; C12N 5/04
[52] U.S. Cl. .......... 800/205; 800/DIG. 42; 800/DIG. 44; 435/69.1; 435/70.1; 435/172.3; 435/419; 536/23.6; 536/24.1
[58] Field of Search .......... 435/69.1, 70.1, 435/172.3, 240.4, 419; 536/24.1, 23.6; 800/205, DIG. 42, DIG. 44

[56] References Cited

U.S. PATENT DOCUMENTS

| | | | |
|---|---|---|---|
| 4,943,674 | 7/1990 | Houck et al. | 800/205 |
| 5,436,393 | 7/1995 | Rocha-Sosa et al. | 800/205 |

OTHER PUBLICATIONS

Bevan et al., Two hundred and Eight Meeting of the Genetical Society 61(2) (1988) "Transcriptional regulation of genes during potato tuberization" p. 280.
Twell et al., Journal of Cellular Biochemistry, Supp. 12C:206 (1988) "Molecular Analysis of the Patatin Gene Family of Potato (*Solanum Tuberosum* L.)".
Lawton et al., Journal of Cellular Biochemistry, Supp. 12C:299 (1988) "Expression of foreign genes in *solanum tuberosum* CVS bintje and desiree".
Jefferson et al., Journal of Cellular Biochemistry, Supp. 11B:57 (1987) "Regulated Expression of a Chimeric Patatin–Glucuonidase Fusion in Tubers and Induced Internode Cutting of Transformed Potato".
Sosa et al., Embo Journal, 8:23–29 (1889) "Both developmental and metabolic signals actiate the promoter of a class 1 patatin gene".
Jaynes et al., Trends Biotechnol 4:314–320 (1986) "Plant protein improvement by genetic engineering: use of synthetic genes".
Twell et al. 1987. Plant Mol. Biol. 9:365–375.
Bevan et al. 1988. Heredity 61(2):280.
Bevan et al. 1986. Nucleic Acids Research 14(11): 4625–4638.
Mignery et al. 1988. Gene 62:27–44.
Koster-Topfer et al. 1989. Mol. Gen. Genet. 219:390–396.
Ganal et al. 1991. Mol. Gen. Genet. 225:501–509.
Park, W. pp. 1–14 In: Mol. Cell. Biol. Potato. Vayda et al., eds., CAB International, Chapter 4.
Paiva et al. 1983. Plant Physiol. 71:161–168.

*Primary Examiner*—David T. Fox
*Attorney, Agent, or Firm*—Curtis, Morris & Safford P C

[57] ABSTRACT

There are described 5' transcriptional regulatory regions of plant genes which ensure sink organ specific expression of cis-linked DNA sequences as well as recombinant double stranded DNA molecules comprising these 5' regulatory regions. Furthermore the present invention relates to a method for producing transgenic plants which show a sink tissue specific expression of a desired DNA sequence.

25 Claims, 5 Drawing Sheets

FIG. 2A

| | | | | | |
|---|---|---|---|---|---|
| TTTAAATCAT | TGTTTTATTT | TCTCTTTCTT | TTTACAGGTA | TAAAAGGTGA | AAATTGAAGC | 60
| AAGATTGATT | GCAAGCTATG | TGTCACCACG | TTATTGATAC | TTTGGAAGAA | ATTTTTACTT | 120
| ATATGTCTTT | GTTTAGGAGT | AATATTTGAT | ATGTTTTAGT | TAGATTTTCT | TGTCATTTAT | 180
| GCTTTAGTAT | AATTTTAGTT | ATTTTTATTA | TATGATCATG | GGTGAATTTT | GATACAAATA | 240
| TTTTTGTCAT | TAAATAAATT | AATTTATCAC | AACTTGATTA | CTTTCAGTGA | CAAAAAATGT | 300
| ATTGTCGTAG | TACCCTTTTT | TGTTGAATAT | ACATATATGT | TTTTATTTG | TGACAATTGT | 360
| AATTGTCACT | ACTTATGATA | ATATTTAGTG | TTTAATCACA | AAATTATTAA | AGCAAACACT | 420
| TTCAGTGACA | AAATAATAGA | TTTAATCACA | AAATTATTAA | CCTTTTTTAT | AATAATAAAT | 480
| TTATCCCTAA | TTTATACATT | TAAGGACAAA | GTATTTTTT | TATATATAAA | AAATAGTCTT | 540
| TAGTGACGAT | CGTAGTGTTG | AGTCTAGAAA | TCATAATGTT | GAATCTAGAA | AAATCTCATG | 600
| CAGTGTAAAA | AAAGGACGTT | CAGTCCATAG | AGGGGGTGTA | TGTGACACCC | 660
| CAACCTCAGC | AAAAGAAAAC | CTCCCTTCAA | CAAGGACATT | TGCGGTGCTA | AACAATTCA | 720
| AGTCTCATCA | CACATATATT | TATTATATAA | TACTAATAAA | GAATAGAAAA | GGAAAGGTAA | 780

FIG. 2B

```
ACATCATTAA ATCGTCTTTG TATATTTTTA GTGACAACTG ATTGACGAAA TCTTTTTCGT   840
CACACAAAAT TTTTAGTGAC GAAACATGAT TTATAGATGA TGAAATTATT TGTCCCTCAT   900
AATCTAATTT GTTGTAGTGA TCATTACTCC TTTGTTTGTT TTATTGTCA TGTTAGTCCA   960
TTAAAAAAAA ATATCTCTCT TCTTATGTAC GTGAATGGTT GGAACGGATC TATTATATAA  1020
TACTAATAAA GAATAGAAAA AGGAAAGTGA GTGAGGTTCG AGGGAGAGAA TCTGTTTAAT  1080
ATCAGAGTCG ATCATGTGTC AATTTTATCG ATATGACCCT AACTTCAACT GAGTTTAACC  1140
AATTCCGATA AGGCGAGAAA TATCATAGTA TTGAGTCTAG AAAAATCTCA TGTAGTGTGG  1200
GGTAAACCTC AGCAAGGACG TTGAGTCCAT AGAGGGGGGT GTATGTGACA CCCCAACCTC  1260
AGCAAAAGAA AACCTCCCCT CAAGAAGGAC ATTGCGGTG CTAAACAATT TCAAGTCTCA  1320
TCACACATAT ATATATATTA TATAATACTA ATAAATAATA GAAAAAGGAA AGGTAAACAT  1380
CACTAACGAC AGTTGCGGTG CAAACTGAGT GAGGTAATAA ACAGCACTAA CTTTTATTGG  1440
TTATGTCAAA CTCAAAGTAA AATTTCTCAA CTTGTTTACG TGCCTATATA TACCATGCTT  1500
GTTATATGCT CAAAGCACCA ACAAAATTT                                    1529
```

1

PLANT PROMOTERS SPECIFIC FOR SINK ORGAN EXPRESSION OF GENES

RELATED APPLICATIONS

This is a continuation-in-part of application Ser. No. 07/995,911 filed Dec. 22, 1992, now U.S. Pat. No. 5,436,393, which was a continuation of application Ser. No. 07/454,363 filed Dec. 21, 1989 and now abandoned.

BACKGROUND OF THE INVENTION

The present invention relates to 5' transcriptional regulatory regions of plant genes which ensure sink organ specific expression of cis-linked DNA sequences as well as to recombinant double stranded DNA molecules comprising these 5' regulatory regions. Furthermore, the present invention relates to a method for producing transgenic plants which show a sink tissue specific expression of a desired DNA sequence.

Because of the continual increasing need for food and raw materials due to the growth in world population, and because of the long-term reduction in areas of land suitable for growing crops, it is becoming increasingly the task for biological research to increase the yields of crops and their food content. An increase of yields can be achieved, among other methods, by manipulating the metabolic pathways leading to the synthesis of storage substances in the harvestable organs of crop plants. Plant organs which store substances of agricultural interest, such as starch, lipids or proteins, are generally known as "sink" organs. Sink tissues are photosynthetically inactive parts of a plant which are dependent on the import of photoassimilates produced in photosynthetically active parts of the plants ("source" tissues) and which are defined as net importers of photosynthetically fixed carbon dioxide. Typical sink organs are for example roots, grains, fruits and tubers.

Since sink organs are storage areas for biologically relevant substances, it would be desirable to be able to modify the expression of genes which control metabolic pathways involved in sink organ substance production and alter the amount of substances which are stored in the sink organs in order to increase the yield of plants. In particular, it is of special interest to be able to express or inhibit the expression of certain gene products specifically in sink organs.

The expression of genes is regulated by DNA sequences located upstream of the transcription initiation site. These DNA sequence regions are called 5' transcriptional regulatory regions or promoters. In order to control the expression of genes in sink organs, a need exists for DNA sequences which ensure the expression of cis-linked DNA sequences specifically in sink tissues and accordingly, there is a great interest in identifying such regulatory DNA sequences.

The identification and isolation of such regulatory DNA sequences first requires the discovery of products which appear specifically in sink organs or sink tissues of the plant. Once the gene corresponding to the product has been identified and isolated, a careful investigation of the sequence, and above all the identification and isolation of the desired 5' transcriptional regulatory regions, is necessary. Suitable models must then be provided and their function must be established through experiments. Identifying such DNA sequences is a challenging project which is subject to substantial pitfalls and uncertainty. There is however substantial interest in the possibility of genetically modifying plants which justifies the substantial expenditure and efforts necessary in identifying transcriptional sequences and manipulating them to determine their utility.

Processes for the genetic modification of dicotyledonous and monocotyledonous plants are known (EP 267159), as well as the following publications of Crouch et al., in: Molecular Form and Function of the Plant Genome, eds. van Vloten-Doting, Groots and Hall, Plenum Publishing Corp. 1985, pp 555–566; Crouch and Sussex, Planta (1981) 153:64–741 Crouch et al., J. Mol. Appl. Genet (1983) 2:273–283; and Simon et al., Plant Molecular Biology (1985) 5: 191–201, in which various forms of storage proteins in *Brassica napus* are described and by Beachy et al., EMBO. J. (1985) 4:3047–3053; Sengupta-Gopalan et al., Proc. Natl. Acad. Sci. USA (1985) 82:3320–3324; Greenwood and Chrispeels, Plant Physiol. (1985) 79:65–71 and Chen et al., Proc. Natl. Acad. Sci. USA (1986) 83:8560–8564, in which studies concerned with seed storage proteins and genetic manipulation are described and by Eckes et al., Mol. Gen. Genet. (1986) 205:14–22 and Fluhr et al., Science (1986) 232:1106–1112, in which genetic manipulation of light inducible plant genes are described.

SUMMARY OF THE INVENTION

It is an object of the present invention to provide 5' transcriptional regulatory regions which ensure sink tissue specific expression of cis-linked DNA sequences, especially in sink organs such as tubers, fruits or storage roots. Preferably these transcriptional regulatory regions are derived from genes coding for patatin proteins belonging to class I patatin genes.

Patatin genes are a family of genes which encode glycoproteins in potato plants. Genes coding for patatin proteins are divided into two classes based on the presence (class II) or absence (class I) of a 22 bp sequence in the 5'-untranslated region (Mignery et al., 1988, Gene 62, 27–44). Various genes belonging to these two classes and the 5' flanking sequences of these genes have already been described (see for example Mignery et al., 1988, Gene 62: 27–44). In particular, Twell and Ooms (1987, Plant Mol. Biol. 9:345–375) showed that 5' transcriptional regulatory regions derived from class II patatin genes cannot ensure significant tuber specific expression of a reporter gene in transgenic potato plants. There has been no other identification of a promoter sequence which can ensure sink organ significant expression.

However, the experiments, described below, surprisingly show that, in contrast to promoters derived from class II patatin genes, the 5' transcriptional regulatory regions derived from class I patatin genes lead to a strong expression of cis-linked DNA sequences in sink tissues of transgenic plants, especially in storage organs such as potato tubers or tomato fruits.

The examples specifically show that a reporter gene fused to the transcriptional regulatory region of a class I patatin gene is specifically expressed to high levels in tubers of transformed potato plants and to a somewhat lower degree in roots. As compared to the constructs described by Twell and Ooms (1987, Plant Mol. Biol. 9: 365–375), which comprise a class II patatin promoter, the expression rate in sink organs of the inventive construct which uses a class I patatin promoter is about 100 times higher.

Furthermore, additional examples of the present invention show that the 5' transcriptional regulatory region of a class I patatin gene of *Solanum tuberosum* leads to the expression of a reporter gene specifically in fruits of transformed tomato plants and to the expression of a reporter gene in hairy roots developed by leaf discs upon transformation with an *Agrobacterium rhizogenes* strain. This data shows that 5' regulatory regions of class I patatin genes of *S. tuberosum* also can ensure sink tissue specific expression across plant species.

Therefore, a 5' transcriptional regulatory region derived from class I patatin genes can be used in the construction of expression cassettes to ensure the expression of any desired DNA sequence specifically in sink tissues of transgenic plants, preferably in storage organs.

An expression cassette is a DNA molecule which in general comprises the following sequences in the 5'-3' transcription direction:

a) a 5' transcriptional regulatory region,
b) a desired DNA sequence to be expressed, and
c) a transcription termination region.

An object of the present invention is therefore to provide recombinant double stranded DNA molecules comprising an expression cassette for the sink tissue specific expression of a DNA sequence, wherein the 5' transcriptional regulatory region ensuring the sink tissue specific expression is derived from a class patatin gene. Preferably the 5' transcriptional regulatory region is derived from one of the class I patatin genes described in Mignery et al. (1988, Gene 62: 27–44), especially from patatin genes PS3,PS7, PS20 and PS23 (GenEMBL data base Accession number: M18881, M18883, M18880 and M18882 respectively), or from patatin PAT21 (Beyan et al., 1986, Nucl. Acids Res. 14: 4625–4638; GenEMBL data base Accession number: X03956), or from patatin gene B24 (Liu et al., 1991, Plant Mol. Biol. 17:1139–1154; GenEMBL data base Accession number: X60396), or from gene pgT16 (Liu et al., 1991, Plant Mol. Biol. 17:1139–1154; GenEMBL data base Accession number:X60399) and most preferably from the class I patatin gene B33 of *Solanum tuberosum* (Rocha-Sosa et al., 1989, EMBO J. 8: 23–31).

In a preferred embodiment of the invention the 5' transcriptional regulatory region comprises the DNA sequence of the region between nucleotides +14 and −1513 of the promoter region of the patatin gene B33 of *Solanum tuberosum* as disclosed in FIG. 2. The 5' transcriptional regulatory region can be native, homologous, to the host plants or foreign, heterologous, to the host plants.

The DNA sequence to be expressed can be homologous or heterologous with respect to the transformed plant and can be fused to the transcriptional regulatory region in sense or anti-sense orientation. The DNA sequence can contain all of the possible open reading frames for a desired peptide as well as one or more introns. Examples include sequences for enzymes; sequences that are complementary (a) to a genome sequence whereby the genome sequence can be an open reading frame; (b) to an intron; (c) to a non-coding leading sequence; (d) to any sequence, which inhibits through complementarity, transcriptional mRNA processing (for example splicing) or translation. The desired DNA sequence can be synthetically produced or extracted naturally, or can contain a mixture of synthetic or natural DNA content. In general, a synthetic DNA sequence is produced with codons which are preferred by the plants. These preferred codons are selected from the codons with the highest protein frequency which can be expressed in the most interesting plant species.

The termination region is optionally exchangeable. Conveniently, the transcription initiation and termination regions in the direction of transcription should be provided by a linker or polylinker which contains one or more restriction positions for the insertion of the DNA sequence. As a rule, the linker has 1–10, usually 1–8, and preferably 2–6 restriction positions. In general the linker has a size of less than 100 bp, usually less than 60 bp, but is, however, at least 5 bp.

The expression cassettes comprising a 5' transcriptional regulatory region of a class I patatin gene followed by a desired DNA sequence can be introduced into plant cells. Regeneration of whole plants from the transformed plant cells leads to the production of transgenic plants expressing the desired DNA sequence specifically in sink tissues.

A further object of the present invention is therefore to provide methods for the production of transgenic plants which show a sink organ specific expression of a desired DNA sequence. Such a method comprises the following steps:

a) construction of an expression cassette comprising the following sequences
  i) a 5' transcriptional regulatory region derived from a class I patatin gene,
  ii) a desired DNA sequence to be expressed and
  iii) a transcription termination region,
b) transfer of this expression cassette into plant cells and
c) regeneration of whole intact plants from the transformed cells.

The expression cassette is preferably constructed as described above.

The transfer of the expression cassette into plant cells is preferably achieved by the use of plant transformation vectors which ensure stable integration of the expression cassette into the plant genome.

In preparing the expression cassettes and inserting the expression cassettes into suitable vector molecules, the different DNA fragments can be manipulated so that the vector contains a DNA sequence which leads generally in the correct direction and which is equipped with the correct reading frame. For ligating the DNA fragments to each other, adaptors or linkers can be introduced on the fragment ends. Further manipulations can be performed to provide the suitable restriction positions or to separate the excess DNA or the restriction positions. Where insertions, deletions or substitutions, such as for example transitions and transversions, are concerned, in vitro mutagenesis, primer repair, restriction or ligation can be used. These manipulations can be performed both in the 5' transcriptional regulatory region, as well as in the DNA sequence which is to be expressed.

In suitable manipulations such as, for example, restriction, "chewing-back" or filling up of overhangs for "blunt-ends", complementary ends of the fragments for the fusing and ligation can be used. It is preferred that in order to carry out the various steps which serve to ensure the expected success of the invention, cloning is used to increase the amount of DNA and for DNA analysis.

Many cloning vectors are available which contain a replication system for *E. coli* and a marker which allows for selection of the transformed cells. The vectors contain for example pBR 332, pUC series, M13 mp series, pACYC 184 etc. Using the systems, the sequence can be introduced into a suitable restriction position in the vector. The contained plasmid is used for the transformation in *E. coli*. The *E. coli* cells are cultivated in a suitable nutrient medium and then harvested and lysed. The plasmid is then recovered. The plasmid can then be analyzed using any standard method of analysis including sequence analysis, restriction analysis, electrophoresis and other biochemical-molecular biological methods. After each manipulation, the DNA sequence which is used can be restricted and then connected with the next DNA sequence. The plasmid sequences can be cloned in the same or different plasmid.

Depending on the method used for the introduction of the desired DNA sequence into plants, additional DNA sequences may be necessary. If for example, the Ti- or Ri-plasmid of the plant cells is used for the transformation, at least the right boundary and often, the right and the left boundaries of the Ti- and Ri-plasmid T-DNA, as flanking areas of the introduced gene, can be connected. The use of T-DNA for the transformation of plant cells is being intensively studied and is well described in EP 120 516; Hoekema, in: The Binary Plant Vector System offsetdrukkerij Kanters B. B., Alblasserdam, 1985, Chapter V; Fraley, et al., Crit. Rev. Plant Sci., 4:1–46 und An et al., EMBO J. (1985) 4:277–284.

When the introduced DNA is first integrated into the genome, it is usually relatively stable and generally does not come out of the genome. The DNA sequence normally contains a selection marker which is passed on to the transformed plant cells, and which confers resistance against a biocide or an antibiotic such as kanamycin, G 418, bleomycin, hygromycin or chloramphenicol, among others. The particular marker employed should be one which will allow for selection of transformed cells as compared to untransformed cells which lack the introduced marker DNA.

A variety of techniques are available for introducing DNA into a plant host cell. These techniques include transformation with T-DNA, using *Agrobacterium tumefaciens* or *Agrobacterium rhizogenes* as the transformation agent, fusion, injection, or electropotation, as well as further possibilities. If Agrobacteria are used for transformation, the introduced DNA must be cloned in special plasmids and either an intermediary vector or a binary vector must be used. The intermediary vectors are based on sequences which are homologous with sequences in the T-DNA and can be integrated through homologous recombination in the Ti- or Ri- plasmid. These also contain the necessary Virregion for the transfer of the T-DNA. Intermediary vectors cannot be replicated in Agrobacteria. By means of helperplasmid, the intermediary vector of Agrobacterium vectors can be replicated in *E. coli* as well as in linker or polylinker, which are framed from the right and left T-DNA border regions. They can be transformed directly in the Agrobacteria (Holsters et al., Mol. Gen. Genet. (1978) 163: 181–187). The Agrobacterium serving as host cells should contain a plasmid that carries the Vir-region since this region is necessary for the transfer of the T-DNA into the plant cells in which additional T-DNA can be contained. The bacterium so transformed is used for the transformation of the plant cells. For the transfer of DNA in the plant cells, plant explanates can be cultivated in suitable manner with *Agrobacterium tumefaciens* or *Agrobacterium rhizogenes*. For the infected plant material (for example leaf bits, stem segments, roots as well as protoplasts or suspensions of cultivated cells), whole plants can then be regenerated in a suitable medium which can contain antibiotics or biocides which are used for selection. The selected plants can then be tested for the presence of introduced DNA. With injection and electroporation methods, there are no special requirements for the plasmid and a simple plasmid, for example a pUC derivative, can be used.

The introduction of foreign genes into plants can be used in a variety of applications. Of special interest is the expression of genes for mammalian products such as, for example, blood factors; lymphokines; colony stimulation factors; interferons; plasminogen activators, enzymes such as for example superoxide dismutase or chymosin; hormone, thioesterase-2 from rat milk or human serum albumin. In addition, these methods and products can be used to increase the amounts of tuber proteins, especially mutated tuber proteins, which have optimized amino acid composition (essential amino acids) and in this way increase the nutritive value of the tubers. Should the amounts of specified endogenous products be reduced, the expression of the gene or parts of this gene in the wrong orientation (anti-sense orientation) to the promoter is also conceivable, leading to the synthesis of an RNA, which is complementary to a total or to parts of an endogenous gene and thus the transcription of this gene or the processing and/or translation of the endogenous mRNA can be inhibited.

The transformed cells grow within the plants in the usual way (see also McCormick et al., Plant Cell Reports (1986) 5, 81–84). The plants can be grown normally and crossed with plants that possess the same transformed gene or other genes. The resulting hybridized plants will have the corresponding phenotypic properties. Two or more generations should be grown, in order to ensure that the phenotypic state remains stable and that the corresponding phenotype or other individual characteristics will be passed on. This is especially important if seeds are to be harvested. There are a large variety of suitable host plants for the sink organ specific expression, particularly tuber forming plant species and more particularly those of the *Solanaceae* species and most especially *Solanum tuberosum*.

The identification of the transcriptional starting regions can be performed in a number of ways. One method is to isolate mRNAs from specific parts of plants (i.e. tubers). It is also possible to further increase the concentration of the mRNA specific to the cells or associated with plant conditions by using cDNA whereby the non-specific cDNA from the mRNA or the cDNA from other tissues or plant conditions (for example wounded/non-wounded) can be drawn off. The remaining cDNA can then be used for probing the genome for complementary sequences using a suitable plant DNA library. Where the protein is to be isolated, it can be partially sequenced so that a probe for direct identification of the corresponding sequences in a plant DNA library can be obtained. The sequences that are hybridized with the probe can then be isolated and manipulated.

Further, the non-translated 5'-region that is associated with the coded area can be isolated and used in expression cassettes for the identification of the transcriptional activity of the non-translated 5'-regions.

The expression cassette obtained, which uses the non-translated 5'-region, can be transformed into plants (see above) in order to test the functionality with a heterologous sequence as well as the sink organ specificity. In this way specific sequences which can direct sink organ specific transcription can be identified.

Expressions and Abbreviations

Abbreviations
d, kd=dalton, kilodalton
bp=Base pairs
cDNA=A copy of a mRNA produced by reverse transcriptase.
mRNA=Messenger ribonucleic acid.
T-DNA=Transfer-DNA (localized on the Ti-plasmid from *Agrobacterium tumefaciens*)

Terms
Blunt Ends=DNA ends in which both DNA strands are exactly the same length.
Chewing-back=Enzymatic removal of nucleotides of a DNA strand which is longer than the complementary strand of a DNA molecule.
Electrophoresis=A biochemical process of separation, for separating nucleic acids from proteins according to size and charge.
Expression=Activity of a gene.
Gene=Genetic factor; a unit of inheritance, carrier of at least part of the information for a particular specified characteristic. Genes consist of nucleic acids (eg DNA, RNA).
Genome=Totality of the genes localized in the chromosomes of the cell.
Genome-sequence=The DNA sequence of the genome whereby three nucleotide bases lying within it form a codon which code again for a specific amino acid.
RNA splicing=A gene does not always show up as a colinear unity but can contain non-coded sequences (introns) which must be spliced from the mRNA (splicing).

7

Heterologous gene(s) or DNA=Foreign genes or foreign DNA.

Homologous gene(s) or DNA=Gene or DNA derived from the same species.

Clone=Cell population that is derived from one of its own mother cells. Descendants are genotypically the same. By cloning, the homogeneity of cell lines can be increased further.

Ligation=Enzymatic formation of a phosphodiester bond between 5'-phosphate groups and 3'-hydroxy groups of the DNA.

Linker, Polylinker=Synthetic DNA sequence that contains one or more (polylinker) restriction cutting regions in direct sequence.

Northern blots.=Transfer and fixing of

Southern blots, electrophoretically separate RNA or DNA on a nitrocellulose or nylon membrane.

Patatin=Trivial name for main storage protein of potato tubers; a glycoprotein of ca. 40 kd molecular weight.

Phenotype=A sum of the characteristics, which are expressed in an organism as opposed to its genotype.

Plasmid=Additional extrachromosomal DNA gene carrier in bacteria cells (possibly also in eukaryons) which reduplicate themselves independently of the bacterial chromosomes. The plasmid can be integrated in other DNA hosts.

Primer=Starting piece; polynucleotide strand on which further nucleotides can be attached.

Promoter=Control sequence of DNA expression which realizes the transcription of homologous or heterologous DNA gene sequences.

Replication=Doubling of the DNA sequence.

Restriction enzymes=Restriction endonucleases that result in particular sub-units of endo DNA-s (for example EcoRI (specificity G↓AATTC and ECORII↓CC((AT) GG, from E. coli); characterized by high specificity of the substrate (↓=splitting position).

Restriction positions=A splitting position which is produced specifically by restriction enzymes.

Termination=A last stage of the protein and/or the RNA synthesis.

Transformation=Introduction of exogenous DNA of a bacterial species into receiver cell.

Transcription=Overwriting on an RNA the genetic information contained in the DNA.

Translation=Translation of the genetic information which is memorized in the form of a linear sequence of bases in nucleic acids. The product of the translation is a polypeptide that comprises a sequence of amino acids.

Transition=Base pair exchange: purine-pyrimidine to purine-pyrimidine e.g. A-T exchanging G-C.

Transversion=Base pair exchange: purine - pyrimidine to pyrimidine-purine e.g. A-T replacing T-A.

Deletion=Removal of one or more base pairs;

Insertion=Introduction of one or more base pairs; Transition, Transversion, Deletion and Insertion are point mutations.

Vectors=Host specific replicatable structures, that take up genes and carry these into other cells. Plasmid can also be used as vectors.

On Dec. 16, 1988, the following microorganism was deposited in accordance with the terms of the Budapest Treaty at the German Collection for Microorganisms (DSM) in Braunschweig. Germany, a recognized depository under the Budapest Treaty (deposit number):

*Agrobacterium tumefaciens* LBA4404, *A. tum.* M 14, containing the plasmid pBI 101-B33 (DSM 5089)

Other features and advantages of the present invention will become apparent from the following description of the invention which refers to the accompanying drawings.

8

Abbreviations

E=Eco RI, H=HindIII, K=KpnI, B=Bam HI, S=SstI, V=Eco RV, X=XbaI, C=ClaI, D=DraI

FIG. 2 shows the nucleic acid sequence (Sequence ID No. 1) of the 5' transcriptional regulatory region of the class I patatin gene B33 of *Solanum tuberosum*. This sequence comprises the nucleotides +14 to −1513 of the gene B33 (Rocha-Sosa et al., 1989, EMBO J.8:23–29; GenEBML database accession number X14483).

Figure 3:
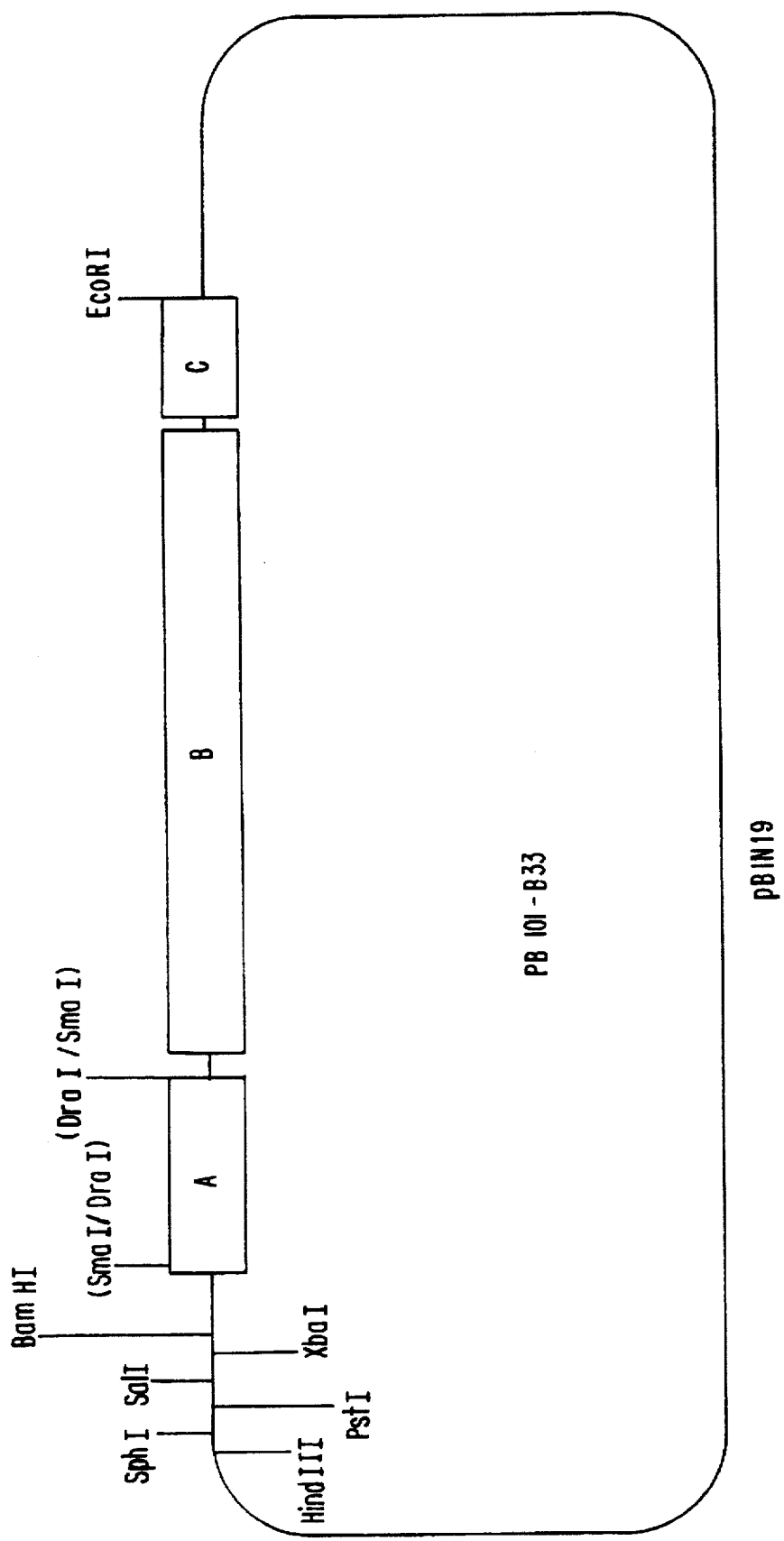

FIG. 3 shows the 13.5 kb long plasmid PB101-B33, comprising the following fragments:

A=Fragment A comprises the 5' regulatory region of the class I patatin gene B33 from *Solanum tuberosun* (nucleotides+14 to −1513) (Rocha-Sosa et al., 1989, EMBO J.8:23–29; GenEBML database accession number X14483)

B=2 kb fragment comprising the coding region for b-glucuronidase (GUS) from *E. coli.*

C=polyadenylation signal of the nopalinsynthase gene

Figure 4:
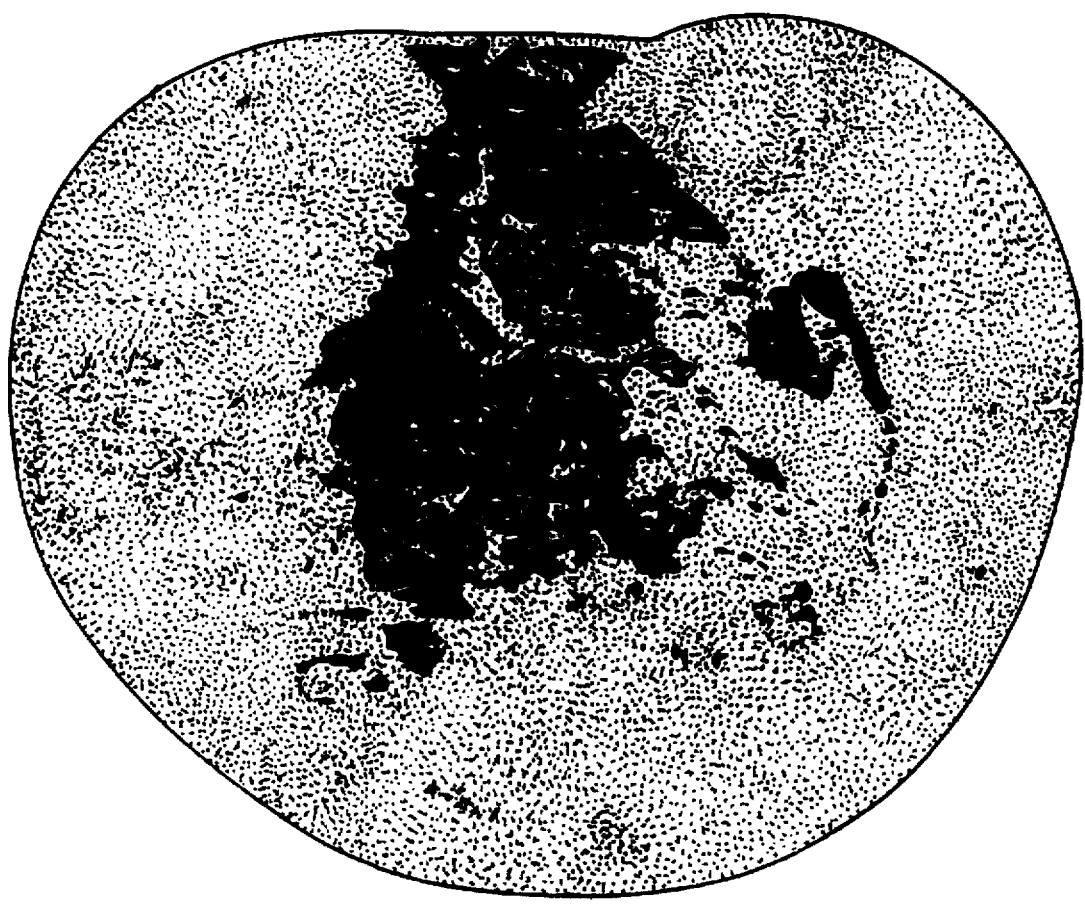

FIG. 4 shows a GUS staining of a cross section of a tomato fruit of a transgenic tomato plant transformed with the plasmid PB101-B33. Dark regions show areas which display GUS activity.

DETAILED DESCRIPTION OF THE INVENTION

For a better understanding of this invention the following examples are given. An explanation for these experiments is given as follows:

1. Cloning Vectors

For cloning, the vectors pUC18/19 (Yanisch-Perron et al Gene (1985), 33, 103–119) were used.

For plant transformations, the gene structures were cloned in the binary vector BIN19 (Beyan, Nucl Acids Research (1984), 12, 8711–8720).

2. Bacterial Species

For the pUC-and M13 vectors, the *E. coli* species BMH71–18 (MEssing et al, Proc. Natl. Acad. Sci. USA (1977), 24, 6342–6346) or TB1 was used. For the vectors pMPK110 and BIN19, the species TB1 was exclusively used. TB1 is a recombinant, negative, 10 tetracyclines resistant derivative of the species JM101 (Yanisch-Perron et al., Gene (1985), 33, 103–119). The genotype of the TB1 species is (Bart Barrel, personal communication): F' (traD36, proAB, lacl, lacZΔM15), A(lac, pro), SupE, thiS, recA, Srl: :Tn10 (TcR). The plant transformation was carried out with the help of the *Agrobacterium tumefaciens* species LBA4404 (Beyan, M., Nucl. Acids Res. 12, 8711–8721 (1984); Bin 19-derivative).

Medium

YT-Medium: 0.5% yeast extract, 0.5% NaCl; 0.8% bactotrypton, if necessary in 1.5% agar.

YEB-Medium: 0.5% beef extract, 0.1% yeast extract, 0.5% peptone, 0.5% saccharose, 2 mMMgSO4, if necessary in 1.5% agar.

MS-Medium: According to Murashige and Skoog (Physiologia Plantarum (1962), 15, 473–497) .

3. Transformation of *Agrobacterium tumefaciens*.

The introduction of the DNA in the Agrobacterium in BIN19-derivatives is carried out by direct transformation by the method of Holsters et al. (Mol. Gen. Genet. (1978), 163, 181–187). The plasmid DNA from transformed agrobacteria are isolated by the method of Birnboim and Doly (Nucl. Acids Res. (1979), 7, 1513–1523) and separated by gel electrophoresis after suitable restriction cleavage.

4. Plant Transformation 10 small leaves of a sterile potato culture, wounded with a scalpel, were put into 10 ml MS-medium with 2% saccharose which contained 30 to 50 of an overnight culture of *Agrobacterium tumefaciens*, washed under selection. After 3–5 minutes gentle shaking, the petri dishes were incubated at 25 C in the dark. After two days, the leaves were laid in MS-medium with 1.6% glucose, 2 mg/l zeatinribose, 0.02 mg/l naphthylacetic acid, 0.02 mg/l gibberellic acid, 500 mg/l claforan, 50 mg/l kanamycin and 0.8% bacto-agar. After one week incubation at 25 C and 3000 lux, the claforan concentration in the medium was reduced by half.

5. Analysis of the Genomic DNA from Transgenic Plants

The isolation of genomic plant DNA was carried out by the method of Rogers and Bendich (Plant Mol. Biol (1985), 5, 69–76).

For DNA analysis, 10–20 μg DNA was tested after suitable restriction cleavage with the aid of Southern blots to determine the integration of the DNA sequences being analyzed.

6. Analysis of the Total RNA from Transgenic Plants

The isolation of the total plant RNA was carried out by the method of Longemann et al (Analytical Biochem (1987), 163, 16–20).

For the analysis, 50 μg samples of total RNA were tested with the use of Northern blots to determine the presence of the sought transcripts.

7. GUS-Test

The activity of the β-glucuronidase (GUS) in transgenic plants was determined by the method of Jefferson (Plant Mol. Biol. Rep. (1987), 5, 387–405). The protein determination was carried out by the method of Bradford (Anal. Biochem. (1976), 72, 248–254). For the determination of the gas activity, 50 μg protein was Used, and incubation was carried out at 37 C for 30 minutes.

The following examples illustrate the isolation and identification of the 5' transcriptional regulatory regions of plant genes. In addition, the examples demonstrate the function and use of class I patatin promoters in sink organs.

EXAMPLE 1

Cloning and Structural Analysis of a Patatin Gene from *Solanum Tuberosum* cDNA clones that code for the patatin protein in potatoes, were isolated and sequenced from the potato variety Berolina (Rosahl et al Mol. Gen. Genetics 203, 214–220 (1986). These cDNA clones then were used to isolate a homologous genomic patatin clone from the potato variety Berolina (Max-Planck-Instut für Zuchtungsforschung, Köln).

EXAMPLE 2

Cloning, Identification and Primary Structure of a Genomic Patatin Clone

Figure 1:
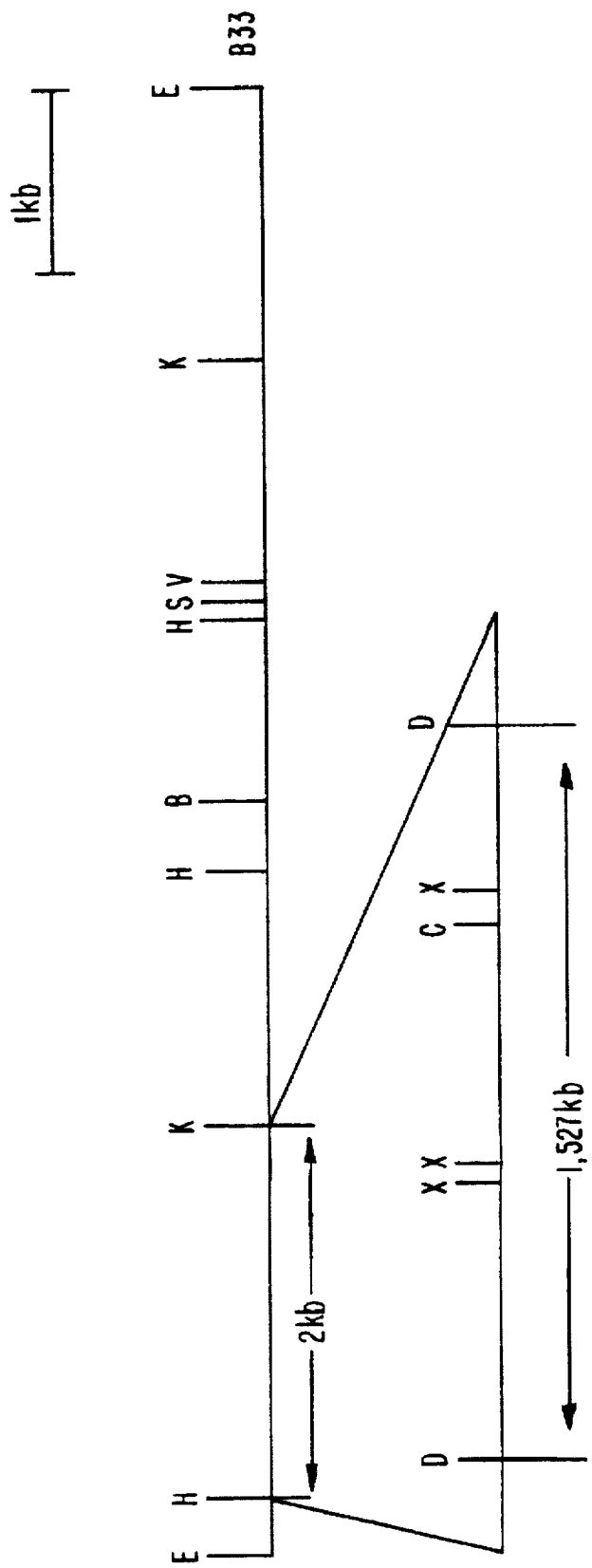
FIG. 1 shows the restriction map of the genomic clone that codes for the potato gene B33.

A genomic library of the nuclear DNA from the potato variety Berolina which was established in the vector from lambda phages EMBL 4 was screened using the patatin cDNA pcT 58. Thirteen independent clones were obtained which were used for the further work after partial sequencing of the clone B33. The restriction map of the clone B33 is shown in FIG. 1. Part of the gene was sequenced and the sequence of the important areas for the transcriptional regulation is given in FIG. 2.

EXAMPLE 3

Identification of the Regulatory Regions Responsible for the Specific Expression of the Patatin Gene B33

A 1,527 kb long DraI/DraI fragment which is located between position+14 and position −1513 (see FIG. 2) was inserted in the SmaI cutting position of the plasmid pB0101 (Jefferson et al, EMBO J. 6, 3901–3907 (1987). In this way, the promoter fragments of the patatin gene B33 with the coded region of the β-glucuronidase from E. coli and the poly-A containing region of the hopaline synthase gene were fused. (see FIG. 3). The fusion of the hopaline synthase terminator takes place on the poly A containing region of the terminator. These constructions were transferred into the Agrobacterium species LBA 4404 (Beyan, M., Nucl. Acids Res. 12, 8711–8721 (1984) and the Agrobacteria containing the chimeric patatin gene was used for transformation of potato leaves. From ten independent containing transformants, in which the presence of the intact nonrearranged chimeric patatin glucuronidase gene was demonstrated, using Southern blot analyses, leaves, stems, tubers and roots were analyzed for activity of β-glucuronidase.

The results are shown in Table 1. From this data, it can be seen that the DraI/DraI fragment of the patatin gene B33 which was fused with the β-glucuronidase gene has a strong sink organ specific activity of β-glucuronidase.

TABLE 1

Glucuronidase of the chimeric B33 glucuronidase gene in various organs of different transgenic potato plants.

| Transformant | Root | Stem | Leaf | Tuber |
|---|---|---|---|---|
| 33G-13 | 137 | 55 | 0 | 16882 |
| 33G-19 | 138 | 7 | 14 | 2047 |
| 33G-21 | 155 | 1034 | 25 | 19471 |
| 33G-23 | 0 | 50 | 0 | 12149 |
| 33G-24 | 0 | 14 | 0 | 4530 |
| 33G-27 | 86 | 8 | 4 | 7284 |
| 33G-38 | 30 | 14 | 6 | 3847 |
| 33G-52 | 69 | 10 | 0 | 2864 |
| 33G-61 | 31 | 10 | 2 | 14916 |
| 33G-62 | 133 | 151 | 24 | 18620 |
| x (Avg) | 76 | 135 | 7.5 | 11948 |
| c. v. Desiree | 0 | 2 | 1 | 0 |

Activities are given in pMol methylumbelliferrol/mg protein/minute. C.v. Desiree shows corresponding activity in an untransformed potato plant.

EXAMPLE 4

Activity of the Class I Patatin Promoter B33 in Transgenic Tomato Plants

In order to analyze the expression pattern and rate of the B33 promoter in transgenic tomato plants, the constructs PB101-B33, described in example 3, were introduced into cells of tomato plants. For this purpose tomato seeds of *Lycopersicon esculentum* cv. Moneymaker and cv. Betterboy were germinated in sterile culture on MS medium supplemented with 3% sucrose (3MS; Murashige and Skoog, 1962, Physiologia Plantarum 15:473–497). For transformation all media contained 0.5% agarose instead of agar. Leaf and stem explants were sectioned in liquid 2MS (MS medium supplemented with 2% sucrose) and then preincubated for 24 h in the dark in a *Nicotiana tabacum* W38 suspension culture feeder layer on solid 3MS containing 1 mg/ml NAA, 0.5 mg/l BAP. Then the explants were submerged in a fresh overnight culture of *Agrobacterium tumefaciens* GV2260 (diluted 1:20 in 2MS) containing the respective constructs, dried on sterile 3 MM paper and transferred back onto the feeder layer plates. After cocultivation for 48 hours in darkness, the explants were washed in liquid 2MS, dried on 3 MM paper and transferred to solid MS medium with 3% sucrose, 2 mg/l zeatin, 500 mg/l claforan, 50 mg/l kanamycin and 500 mg/l carbenicillin for regeneration. The explants were transferred to fresh medium every week. Root induction was achieved on solid MS medium containing 3% sucrose and 250 mg/l claforan. Finally, the plantlets were transferred to soil. After acclimatization in a growth chamber, plants were cultivated in the greenhouse. Transformants were tested on Southern level for the presence of intact copies of the respective constructs.

According to the transformation protocol, three transformants were analyzed for GUS activity. GUS activity was determined in leaves and stems of plantlets grown in tissue culture as well as of roots, leaves, stems and fruit of plants grown in the greenhouse. No GUS activity was found in leaves and stems of plantlets grown in tissue culture on media containing 2% sucrose. Furthermore, in plants grown in the greenhouse, no or low levels of GUS activity can be found in roots, leaves or stems. In fully grown transformed plants, GUS activity was only observed in green fruits. No endogenous GUS activity was detectable in any tissues including fruits of non-transformed plants of *Lycopersicon esculentum* cv. Moneymaker and cv. Betterboy. There was no GUS activity detected by the assays, which were performed in 100 mM Tris/HCl pH 7.6, 20% methanol, 10 mM ascorbate, even after 24 hours. In contrast, in the case of the transformants, the first detectable activity in green fruits was already visible after 15 minutes. In green fruits of transgenic tomato plants, a high level of GUS activity was found in the detectable central part of the fruit (see FIG. 4). The pattern of the expression of GUS was variable, reaching from a relatively uniform staining of the fruit tissue to gradient-like patterns between the pedicel and the seeds. No change in the level of GUS activity is found in mature red fruit.

EXAMPLE 5

Activity of a Class I Patatin Promoter in Hairy Roots Developed by Transformed Leaf Discs In order to test whether or not a class I patatin promoter would ensure expression of a cis-linked DNA sequence in roots, the vector PB101-B33 (described in example 3) was transferred into the *Agrobacterium rhizogenes* strain 15834 by direct transformation (Holsters et al., 1978, Mol. Gen. Genet. 163:181–187). The Agrobacterium strain was then used to transform leaf discs of plants.

The infection of plant tissues with *Agrobacterium rhizogenes* results in the production of so called "hairy roots" (Ri-roots) at the site of infection. These roots differ in growth characteristics from roots normally developed by plants but are regarded as a typical sink tissue. In the experiment, leaf tissue of axenically grown sugar beet plants was kept on medium according to Murashige and Skoog (1962, Physiologia Plantarum 15:473–497) supplemented with 2% sucrose (called 2MS medium), 0.4 mg/l Benzyl-amino-purine and 0.1 mg/l Indole-acetic-acid. The leaf tissue was cut into 2 cm square pieces and infected with the *Agrobacterium rhizogenes* 15834 which contained the plasmid PB101-B33. Leaf explants were kept for two days on hormone-free 2MS medium and subsequently incubated in the dark for several weeks on hormone-free 2MS medium containing 500 mg/l claforan.

After 2–4 weeks the transgenic leaf discs developed hairy roots. These roots were stained for b-glucuronidase activity according to Jefferson et al. (1987, Plant. Mol. Biol. Reporter 5:387–405). More than 50% of a population of 100 roots tested stained blue whereas control roots obtained by infection of sugar beet leaves with the *Agrobacterium rhizogenes* strain 15834 devoid of the PB101-B33 plasmid did not show any staining among 100 roots tested.

Although the present invention has been described in relation to particular embodiments thereof, many other variations and modifications and other uses will become apparent to those skilled in the art.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1529 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Solanum tuberosum
        ( F ) TISSUE TYPE: tuber ( v i i ) IMMEDIATE SOURCE:
        ( B ) CLONE: B33

( x i ) SEQUENCE DESCRIPTION: SEQ ID NO:1:

```
TTTAAATCAT TGTTTTATTT TCTCTTTCTT TTTACAGGTA TAAAAGGTGA AAATTGAAGC      60
AAGATTGATT GCAAGCTATG TGTCACCACG TTATTGATAC TTTGGAAGAA ATTTTTACTT     120
ATATGTCTTT GTTAGGAGT  AATATTTGAT ATGTTTAGT  TAGATTTTCT TGTCATTTAT     180
GCTTTAGTAT AATTTTAGTT ATTTTATTA  TATGATCATG GGTGAATTTT GATACAAATA     240
TTTTTGTCAT TAAATAAATT AATTTATCAC AACTTGATTA CTTTCAGTGA CAAAAAATGT     300
ATTGTCGTAG TACCCTTTTT TGTTGAATAT GAATAATTTT TTTTATTTTG TGACAATTGT     360
AATTGTCACT ACTTATGATA ATATTTAGTG ACATATATGT CGTCGGTAAA AGCAAACACT     420
TTCAGTGACA AAATAATAGA TTTAATCACA AAATTATTAA CCTTTTTTAT AATAATAAAT     480
TTATCCCTAA TTTATACATT TAAGGACAAA GTATTTTTTT TATATATAAA AAATAGTCTT     540
TAGTGACGAT CGTAGTGTTG AGTCTAGAAA TCATAATGTT GAATCTAGAA AAATCTCATG     600
CAGTGTAAAA TAAACCTCAA AAAGGACGTT CAGTCCATAG AGGGGGTGTA TGTGACACCC     660
CAACCTCAGC AAAAGAAAAC CTCCCTTCAA CAAGGACATT TGCGGTGCTA AACAATTTCA     720
AGTCTCATCA CACATATATT TATTATATAA TACTAATAAA GAATAGAAAA GGAAAGGTAA     780
ACATCATTAA ATCGTCTTTG TATATTTTA  GTGACAACTG ATTGACGAAA TCTTTTTCGT     840
CACACAAAAT TTTTAGTGAC GAAACATGAT TTATAGATGA TGAAATTATT TGTCCCTCAT     900
AATCTAATTT GTTGTAGTGA TCATTACTCC TTTGTTTGTT TTATTTGTCA TGTTAGTCCA     960
TTAAAAAAAA ATATCTCTCT TCTTATGTAC GTGAATGGTT GGAACGGATC TATTATATAA    1020
TACTAATAAA GAATAGAAAA AGGAAAGTGA GTGAGGTTCG AGGGAGAGAA TCTGTTTAAT    1080
ATCAGAGTCG ATCATGTGTC AATTTTATCG ATATGACCCT AACTTCAACT GAGTTTAACC    1140
AATTCCGATA AGGCGAGAAA TATCATAGTA TTGAGTCTAG AAAAATCTCA TGTAGTGTGG    1200
GGTAAACCTC AGCAAGGACG TTGAGTCCAT AGAGGGGGGT GTATGTGACA CCCCAACCTC    1260
AGCAAAAGAA AACCTCCCCT CAAGAAGGAC ATTTGCGGTG CTAAACAATT TCAAGTCTCA    1320
TCACACATAT ATATATATTA TAATACTA   ATAAATAATA GAAAAGGAA  AGGTAAACAT    1380
CACTAACGAC AGTTGCGGTG CAAACTGAGT GAGGTAATAA ACAGCACTAA CTTTTATTGG    1440
TTATGTCAAA CTCAAAGTAA AATTTCTCAA CTTGTTTACG TGCCTATATA TACCATGCTT    1500
GTTATATGCT CAAAGCACCA ACAAAATTT                                      1529
```

We claim:

1. A process for the production of a transgenic plant having a higher level of expression of a DNA sequence of heterologous origin in a sink organ relative to other tissues of the plant, comprising the following steps:

a) producing an expression cassette having the following sequences:

i) a promoter sequence of a class I patatin gene which leads to a sink organ specific expression of sequences fused to said promoter sequence, ii) a DNA sequence of heterologous origin, which is fused to said promoter sequence, and iii) a DNA sequence for transcriptional and translational termination;

b) transferring the expression cassette into a plant cell thereby producing a transformed plant cell; and c) regenerating a whole, intact transgenic plant from the transformed plant cell, wherein the transgenic plant has a higher level of expression of the DNA sequence of heterologous origin in the sink organ relative to other tissues of the plant.

2. The process according to claim 1, wherein the expression cassette is transferred into the plant cell using recombinant plasmids.

3. A process according to claim 1, wherein the class I patatin promoter sequence comprises Sequence ID No. 1:

| 1   | TTTAAATCAT | TGTTTTATTT | TCTCTTTCTT | TTTACAGGTA | TAAAAGGTGA |
| 51  | AAATTGAAGC | AAGATTGATT | GCAAGCTATG | TGTCACCACG | TTATTGATAC |
| 101 | TTTGGAAGAA | ATTTTTACTT | ATATGTCTTT | GTTAGGAGT  | AATATTTGAT |

-continued

| | | | | | |
|---|---|---|---|---|---|
| 151 | ATGTTTTAGT | TAGATTTTCT | TGTCATTTAT | GCTTTAGTAT | AATTTTAGTT |
| 201 | ATTTTTATTA | TATGATCATG | GGTGAATTTT | GATACAAATA | TTTTTGTCAT |
| 251 | TAAATAAATT | AATTTATCAC | AACTTGATTA | CTTTCAGTGA | CAAAAAATGT |
| 301 | ATTGTCGTAG | TACCCTTTTT | TGTTGAATAT | GAATAATTTT | TTTTATTTTG |
| 351 | TGACAATTGT | AATTGTCACT | ACTTATGATA | ATATTTAGTG | ACATATATGT |
| 401 | CGTCGGTAAA | AGCAAACACT | TTCAGTGACA | AAATAATAGA | TTTAATCACA |
| 451 | AAATTATTAA | CCTTTTTTAT | AATAATAAAT | TTATCCCTAA | TTTATACATT |
| 501 | TAAGGACAAA | GTATTTTTTT | TATATATAAA | AAATAGTCTT | TAGTGACGAT |
| 551 | CGTAGTGTTG | AGTCTAGAAA | TCATAATGTT | GAATCTAGAA | AAATCTCATG |
| 601 | CAGTGTAAAA | TAAACCTCAA | AAAGGACGTT | CAGTCCATAG | AGGGGGTGTA |
| 651 | TGTGACACCC | CAACCTCAGC | AAAAGAAAAC | CTCCCTTCAA | CAAGGACATT |
| 701 | TGCGGTGCTA | AACAATTTCA | AGTCTCATCA | CACATATATT | TATTATATAA |
| 751 | TACTAATAAA | GAATAGAAAA | GGAAAGGTAA | ACATCATTAA | ATCGTCTTTG |
| 801 | TATATTTTTA | GTGACAACTG | ATTGACGAAA | TCTTTTTCGT | CACACAAAAT |
| 851 | TTTTAGTGAC | GAAACATGAT | TTATAGATGA | TGAAATTATT | TGTCCCTCAT |
| 901 | AATCTAATTT | GTTGTAGTGA | TCATTACTCC | TTTGTTTGTT | TTATTTGTCA |
| 951 | TGTTAGTCCA | TTAAAAAAAA | ATATCTCTCT | TCTTATGTAC | GTGAATGGTT |
| 1001 | GGAACGGATC | TATTATATAA | TACTAATAAA | GAATAGAAAA | AGGAAAGTGA |
| 1051 | GTGAGGTTCG | AGGGAGAGAA | TCTGTTTAAT | ATCAGAGTCG | ATCATGTGTC |
| 1101 | AATTTTATCG | ATATGACCCT | AACTTCAACT | GAGTTTAACC | AATTCCGATA |
| 1151 | AGGCGAGAAA | TATCATAGTA | TTGAGTCTAG | AAAAATCTCA | TGTAGTGTGG |
| 1201 | GGTAAACCTC | AGCAAGGACG | TTGAGTCCAT | AGAGGGGGGT | GTATGTGACA |
| 1251 | CCCCAACCTC | AGCAAAAGAA | AACCTCCCCT | CAAGAAGGAC | ATTTGCGGTG |
| 1301 | CTAAACAATT | TCAAGTCTCA | TCACACATAT | ATATATATTA | TATAATACTA |
| 1351 | ATAAATAATA | GAAAAAGGAA | AGGTAAACAT | CACTAACGAC | AGTTGCGGTG |
| 1401 | CAAACTGAGT | GAGGTAATAA | ACAGCACTAA | CTTTTATTGG | TTATGTCAAA |
| 1451 | CTCAAAGTAA | AATTTCTCAA | CTTGTTTACG | TGCCTATATA | TACCATGCTT |
| 1501 | GTTATATGCT | CAAAGCACCA | ACAAAATTT. | | |

4. A process according to claim 1, wherein the class I patatin promoter sequence is the B33 promoter sequence derived from *Solanum tuberosum*.

5. A process according to claim 4, wherein the class I patatin promoter sequence is the DraI/DraI fragment located between position +14 and position −1513 of the KpnI/Hind III sequence shown in FIG. 2.

6. A process according to claim 4, wherein the transgenic plant expresses the DNA sequence of heterologous origin at a level at least 100 times higher in the sink organ relative to the other tissues.

7. A process according to claim 1, wherein said DNA sequence of heterologous origin encodes a peptide.

8. A process according to claim 1, wherein said plant cell is a potato cell and said plant is a potato plant.

9. A process according to claim 8, wherein said DNA sequence of heterologous origin encodes a peptide.

10. A process according to claim 1, wherein said plant cell is a tomato cell and said plant is a tomato plant.

11. The process according to claim 10, wherein the expression cassette is transferred into said tomato cell using recombinant plasmids.

12. A process according to claim 10, wherein said class I patatin promoter sequence comprises Sequence ID No. 1:

| | | | | | |
|---|---|---|---|---|---|
| 1 | TTTAAATCAT | TGTTTTATTT | TCTCTTTCTT | TTTACAGGTA | TAAAAGGTGA |
| 51 | AAATTGAAGC | AAGATTGATT | GCAAGCTATG | TGTCACCACG | TTATTGATAC |
| 101 | TTTGGAAGAA | ATTTTTACTT | ATATGTCTTT | GTTTAGGAGT | AATATTTGAT |
| 151 | ATGTTTTAGT | TAGATTTTCT | TGTCATTTAT | GCTTTAGTAT | AATTTTAGTT |
| 201 | ATTTTTATTA | TATGATCATG | GGTGAATTTT | GATACAAATA | TTTTTGTCAT |
| 251 | TAAATAAATT | AATTTATCAC | AACTTGATTA | CTTTCAGTGA | CAAAAAATGT |
| 301 | ATTGTCGTAG | TACCCTTTTT | TGTTGAATAT | GAATAATTTT | TTTTATTTTG |
| 351 | TGACAATTGT | AATTGTCACT | ACTTATGATA | ATATTTAGTG | ACATATATGT |
| 401 | CGTCGGTAAA | AGCAAACACT | TTCAGTGACA | AAATAATAGA | TTTAATCACA |
| 451 | AAATTATTAA | CCTTTTTTAT | AATAATAAAT | TTATCCCTAA | TTTATACATT |
| 501 | TAAGGACAAA | GTATTTTTTT | TATATATAAA | AAATAGTCTT | TAGTGACGAT |
| 551 | CGTAGTGTTG | AGTCTAGAAA | TCATAATGTT | GAATCTAGAA | AAATCTCATG |
| 601 | CAGTGTAAAA | TAAACCTCAA | AAAGGACGTT | CAGTCCATAG | AGGGGGTGTA |
| 651 | TGTGACACCC | CAACCTCAGC | AAAAGAAAAC | CTCCCTTCAA | CAAGGACATT |
| 701 | TGCGGTGCTA | AACAATTTCA | AGTCTCATCA | CACATATATT | TATTATATAA |
| 751 | TACTAATAAA | GAATAGAAAA | GGAAAGGTAA | ACATCATTAA | ATCGTCTTTG |
| 801 | TATATTTTTA | GTGACAACTG | ATTGACGAAA | TCTTTTTCGT | CACACAAAAT |
| 851 | TTTTAGTGAC | GAAACATGAT | TTATAGATGA | TGAAATTATT | TGTCCCTCAT |
| 901 | AATCTAATTT | GTTGTAGTGA | TCATTACTCC | TTTGTTTGTT | TTATTTGTCA |
| 951 | TGTTAGTCCA | TTAAAAAAAA | ATATCTCTCT | TCTTATGTAC | GTGAATGGTT |
| 1001 | GGAACGGATC | TATTATATAA | TACTAATAAA | GAATAGAAAA | AGGAAAGTGA |
| 1051 | GTGAGGTTCG | AGGGAGAGAA | TCTGTTTAAT | ATCAGAGTCG | ATCATGTGTC |
| 1101 | AATTTTATCG | ATATGACCCT | AACTTCAACT | GAGTTTAACC | AATTCCGATA |
| 1151 | AGGCGAGAAA | TATCATAGTA | TTGAGTCTAG | AAAAATCTCA | TGTAGTGTGG |
| 1201 | GGTAAACCTC | AGCAAGGACG | TTGAGTCCAT | AGAGGGGGGT | GTATGTGACA |
| 1251 | CCCCAACCTC | AGCAAAAGAA | AACCTCCCCT | CAAGAAGGAC | ATTTGCGGTG |
| 1301 | CTAAACAATT | TCAAGTCTCA | TCACACATAT | ATATATATTA | TATAATACTA |
| 1351 | ATAAATAATA | GAAAAAGGAA | AGGTAAACAT | CACTAACGAC | AGTTGCGGTG |
| 1401 | CAAACTGAGT | GAGGTAATAA | ACAGCACTAA | CTTTTATTGG | TTATGTCAAA |

-continued

| 1451 | CTCAAAGTAA | AATTTCTCAA | CTTGTTTACG | TGCCTATATA | TACCATGCTT |
| 1501 | GTTATATGCT | CAAAGCACCA | ACAAAATTT. | | |

13. A process according to claim 10, wherein the class I patatin promoter sequence is the B33 promoter sequence derived from Solanum tuberosum.

14. A process according to claim 10, wherein the class I patatin promoter sequence is the DraI/DraI fragment located between position +14 and position −1513 of the KpnI/Hind III sequence shown in FIG. 2.

15. A process according to claim 13, wherein the transgenic plant expresses the DNA sequence of heterologous origin at a level at least 100 times higher in the sink organ relative to the other tissues.

16. A process according to claim 10, wherein said DNA sequence of heterologous origin encodes a peptide.

17. A transgenic plant comprising an expression cassette comprising the following sequences:
 i) a promoter sequence of a class I patatin gene which leads to a sink organ specific expression of sequences fused to said promoter sequence,
 ii) a DNA sequence of heterologous origin, which is fused to the promoter sequence, and
 iii) a DNA sequence for transcriptional and translational termination, wherein the transgenic plant expresses the DNA sequence of heterologous origin at a level higher in the sink organ relative to the other tissues.

18. A transgenic plant according to claim 17, wherein the class I patatin promoter sequence comprises Sequence ID No. 1:

20. A transgenic plant according to claim 17, wherein the class I patatin promoter sequence is the DraI/DraI fragment located between position +14 and position −1513 of the KpnI/Hind III sequence shown in FIG. 2.

21. A transgenic plant according to claim 17, wherein said transgenic plant is a potato plant.

22. A transgenic plant according to claim 17, wherein said transgenic plant is a tomato plant.

23. A transgenic plant according to claim 17, wherein the expression in the sink organs is at least 100 times higher than the expression in the other tissues.

24. A process for the production of a transformed cell capable of producing a higher level of expression of a DNA sequence of heterologous origin in a sink organ relative to other tissues, comprising the following steps:
 a) producing an expression cassette having the following sequences:
  i) a promoter sequence of a class I patatin gene which leads to a sink organ specific expression of sequences fused to said promoter sequence,
  ii) a DNA sequence of heterologous origin, which is fused to said promoter sequence, and
  iii) a DNA sequence for transcriptional and translational termination; and
 b) transferring the expression cassette into a plant cell thereby producing a transformed plant cell.

25. A transformed cell comprising an expression cassette comprising the following sequences:

| 1 | TTTAAATCAT | TGTTTTATTT | TCTCTTTCTT | TTTACAGGTA | TAAAAGGTGA |
| 51 | AAATTGAAGC | AAGATTGATT | GCAAGCTATG | TGTCACCACG | TTATTGATAC |
| 101 | TTTGGAAGAA | ATTTTTACTT | ATATGTCTTT | GTTTAGGAGT | AATATTTGAT |
| 151 | ATGTTTTAGT | TAGATTTTCT | TGTCATTTAT | GCTTTAGTAT | AATTTTAGTT |
| 201 | ATTTTTATTA | TATGATCATG | GGTGAATTTT | GATACAAATA | TTTTTGTCAT |
| 251 | TAAATAAATT | AATTTATCAC | AACTTGATTA | CTTTCAGTGA | CAAAAAATGT |
| 301 | ATTGTCGTAG | TACCCTTTTT | TGTTGAATAT | GAATAATTTT | TTTTATTTTG |
| 351 | TGACAATTGT | AATTGTCACT | ACTTATGATA | ATATTTAGTG | ACATATATGT |
| 401 | CGTCGGTAAA | AGCAAACACT | TTCAGTGACA | AAATAATAGA | TTTAATCACA |
| 451 | AAATTATTAA | CCTTTTTTAT | AATAATAAAT | TTATCCCTAA | TTTATACATT |
| 501 | TAAGGACAAA | GTATTTTTTT | TATATATAAA | AAATAGTCTT | TAGTGACGAT |
| 551 | CGTAGTGTTG | AGTCTAGAAA | TCATAATGTT | GAATCTAGAA | AAATCTCATG |
| 601 | CAGTGTAAAA | TAAACCTCAA | AAAGGACGTT | CAGTCCATAG | AGGGGGTGTA |
| 651 | TGTGACACCC | CAACCTCAGC | AAAAGAAAAC | CTCCCTTCAA | CAAGGACATT |
| 701 | TGCGGTGCTA | AACAATTTCA | AGTCTCATCA | CACATATATT | TATTATATAA |
| 751 | TACTAATAAA | GAATAGAAAA | GGAAAGGTAA | ACATCATTAA | ATCGTCTTTG |
| 801 | TATATTTTTA | GTGACAACTG | ATTGACGAAA | TCTTTTTCGT | CACACAAAAT |
| 851 | TTTTAGTGAC | GAAACATGAT | TTATAGATGA | TGAAATTATT | TGTCCCTCAT |
| 901 | AATCTAATTT | GTTGTAGTGA | TCATTACTCC | TTTGTTTGTT | TTATTTGTCA |
| 951 | TGTTAGTCCA | TTAAAAAAAA | ATATCTCTCT | TCTTATGTAC | GTGAATGGTT |
| 1001 | GGAACGGATC | TATTATATAA | TACTAATAAA | GAATAGAAAA | AGGAAAGTGA |
| 1051 | GTGAGGTTCG | AGGGAGAGAA | TCTGTTTAAT | ATCAGAGTCG | ATCATGTGTC |
| 1101 | AATTTTATCG | ATATGACCCT | AACTTCAACT | GAGTTTAACC | AATTCCGATA |
| 1151 | AGGCGAGAAA | TATCATAGTA | TTGAGTCTAG | AAAAATCTCA | TGTAGTGTGG |
| 1201 | GGTAAACCTC | AGCAAGGACG | TTGAGTCCAT | AGAGGGGGGT | GTATGTGACA |
| 1251 | CCCCAACCTC | AGCAAAAGAA | AACCTCCCCT | CAAGAAGGAC | ATTTGCGGTG |
| 1301 | CTAAACAATT | TCAAGTCTCA | TCACACATAT | ATATATATTA | TATAATACTA |
| 1351 | ATAAATAATA | GAAAAAGGAA | AGGTAAACAT | CACTAACGAC | AGTTGCGGTG |
| 1401 | CAAACTGAGT | GAGGTAATAA | ACAGCACTAA | CTTTTATTGG | TTATGTCAAA |
| 1451 | CTCAAAGTAA | AATTTCTCAA | CTTGTTTACG | TGCCTATATA | TACCATGCTT |
| 1501 | GTTATATGCT | CAAAGCACCA | ACAAAATTT. | | |

19. A transgenic plant according to claim 17, wherein the class I patatin promoter sequence is the B33 promoter sequence derived from Solanum tuberosum.

i) a promoter sequence of a class I patatin gene which leads to a sink organ specific expression of sequences fused to said promoter sequence, ii) a DNA sequence of heterologous origin, which is fused to the promoter sequence, and iii) a DNA sequence for transcriptional and translational termination, wherein the transformed cell is capable of producing a higher level of expression of the DNA sequence of heterologous origin in a sink organ relative to other tissues.

* * * * *